(12) United States Patent
Grasman et al.

(10) Patent No.: US 12,385,898 B2
(45) Date of Patent: Aug. 12, 2025

(54) IN-VITRO CONTRACTILE FORCE INDICATOR

(71) Applicant: New Jersey Institute of Technology, Newark, NJ (US)

(72) Inventors: Jonathan Grasman, West Orange, NJ (US); Jessica Pridmore, Colts Neck, NJ (US); Cassandra Martin, Barnegat, NJ (US); Katherine Coombs, Oaklyn, NJ (US); Sydnee Sicherer, Newark, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 386 days.

(21) Appl. No.: 17/884,983

(22) Filed: Aug. 10, 2022

(65) Prior Publication Data

US 2023/0051082 A1 Feb. 16, 2023

Related U.S. Application Data

(60) Provisional application No. 63/231,439, filed on Aug. 10, 2021.

(51) Int. Cl.
*G01N 33/483* (2006.01)
*C12M 1/32* (2006.01)
(Continued)

(52) U.S. Cl.
CPC ......... *G01N 33/4833* (2013.01); *C12M 23/12* (2013.01); *C12M 41/40* (2013.01); *G02B 21/26* (2013.01); *G02B 21/365* (2013.01)

(58) Field of Classification Search
CPC .................................................. G01N 33/4833
See application file for complete search history.

(56) References Cited

U.S. PATENT DOCUMENTS 10,725,021 B2 7/2020 Parker et al.
2017/0260488 A1* 9/2017 Costa .................. C12M 41/48

FOREIGN PATENT DOCUMENTS

WO WO-2014085933 A1 * 6/2014 ............... A61F 2/02

OTHER PUBLICATIONS

Machine translation of WO2014085933 (Year: 2014).*
(Continued)

*Primary Examiner* — Walter L Lindsay, Jr.
*Assistant Examiner* — Andrew V Do
(74) *Attorney, Agent, or Firm* — Lerner David LLP

(57) ABSTRACT

Devices and methods to measure cells and/or tissue's contractile force are disclosed. Included is a mount with rigid, and non-rigid posts sized to flex. Determined is force exerted by contractile cells and tissues in a multiwell plate. The device is designed to fit inside individual wells with posts directed downwards. Posts are attached to a 3D printed circular mount with tabs for depth within the well. The mount has a window for medium changes while the device is positioned inside the well. The cells are seeded within a hydrogel. As the hydrogel condenses, cells/tissue wrap around the post's outside pulling non-rigid post toward rigid post. Inverted light microscope is used to determine deflection of non-rigid post inside the multiwell plate. Movement of the non-rigid post is measured using an acrylic ruler on an underside of the multiwell plate. Contractile forces of cells/tissue are determined using cantilever mechanics.

18 Claims, 5 Drawing Sheets

(51) Int. Cl.
*C12M 1/34* (2006.01)
*G02B 21/26* (2006.01)
*G02B 21/36* (2006.01)

(56) References Cited

OTHER PUBLICATIONS

Vandenburgh, Herman et al. "Automated drug screening with contractile muscle tissue engineered from dystrophic myoblasts." FASEB journal : official publication of the Federation of American Societies for Experimental Biology vol. 23,10 (Oct. 2009): 3325-34. doi:10.1096/fj.09-134411.

Agrawal, G. et al., "Skeletal muscle-on-a-chip: an in vitro model to evaluate tissue formation and injuryt", Lab Chip., Oct. 11, 2017, pp. 3447-3461, vol. 17, No. 20, HHS Public Access.

Fitzgerald, M. L. et al., "The relationship between the Young's modulus and dry etching rate of polydimethylsiloxane (PDMS)" Biomedical Microdevices, Mar. 2, 2019, 8 pages, vol. 21, No. 26, Springer. [Abstract Only].

\* cited by examiner

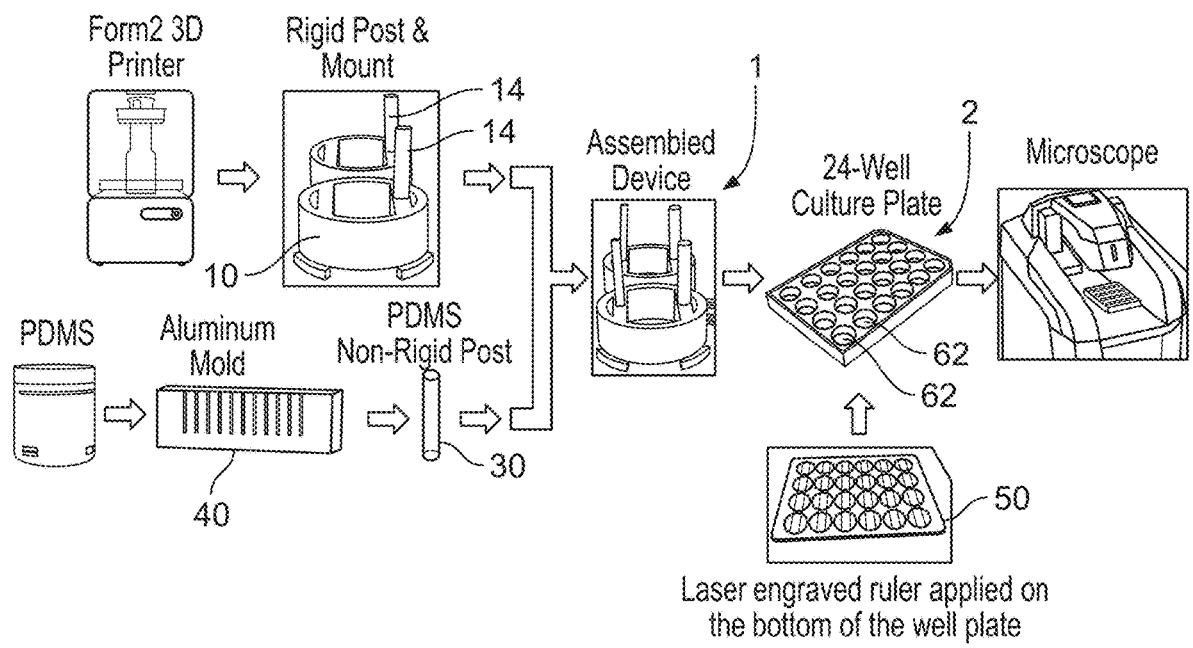
Figure 1
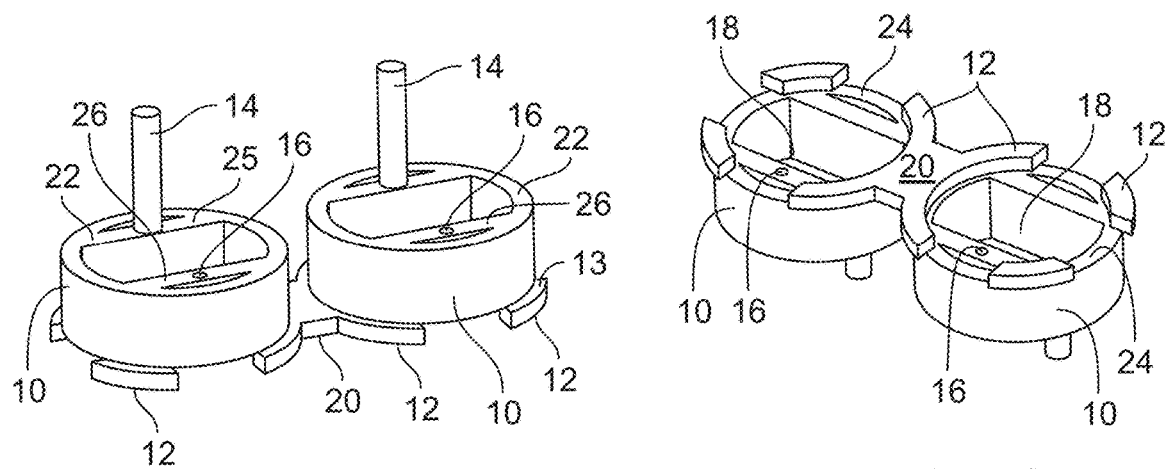
Figure 2A
Figure 2B

IN-VITRO CONTRACTILE FORCE INDICATOR

CROSS-REFERENCE TO RELATED APPLICATION

The present application claims the benefit of the filing date of U.S. Provisional Patent Application No. 63/231,439, filed Aug. 10, 2021, the disclosures of which are hereby incorporated herein by reference.

FIELD OF THE DISCLOSURE

The present disclosure relates to a system and method to measure the contractile force of a cell and tissue. More particularly, the present disclosure is directed to a device that determines the contractile forces that cells and tissues exert in vitro for drug discovery of pharmaceuticals to treat muscular dystrophy and other related diseases present in contractile tissues.

BACKGROUND

Identification and evaluation of new therapeutic agents or identification of suspect disease typically employ animal models that are expensive, time consuming, require skilled animal-trained staff, and utilize large numbers of animals. Pharmaceutical and biotechnical companies have relied on in vitro alternatives that use conventional cell culture systems. These conventional cell culture systems are limited in that they do not allow three-dimensional interactions that occur between cells and surrounding tissue. This drawback is a considerable disadvantage as such interactions are well documented as having a noteworthy influence on the growth and activity of cells in vivo because in vivo cells divide and interconnect in the formation of complex biological systems creating structure-function hierarchies that range from the nanometer to meter scales.

Efforts to build biosynthetic materials or engineered tissues that recapitulate these structure-function relationships often fail because of the inability to replicate the in vivo conditions that coax this behavior from ensembles of cells. For example, engineering a functional muscle tissue requires that the sarcomere and myofibrillogenesis are controlled at the micron length scale, while cellular alignment and formation of the continuous tissue require organizational cues over the millimeter to centimeter length scale.

Biological cells and tissues are dynamic as they could compact and contract by generating force through reorganization of their cytoskeleton and their environment. This ability to contract is critical to develop and maintain cells and tissues. Such contraction allows cells and tissues to undergo dynamic remodeling to maintain homeostasis. In addition, such contraction provides physical support to maintain tissue integrity. The loss of an appropriate level of contractive force could lead to abnormalities or failure of in vitro cultured tissues.

It would be desirable to measure the contractile force of cells and tissues in vitro to understand and predict how interventions may affect these dynamic processes for tissue development or regeneration and screening of numerous drug compounds for cell and tissue interactions.

Accordingly, there is a need for improved methods and systems that may be used for determining the effect of a test compound on biologically relevant parameters in order to enhance and speed-up the drug discovery and development process

SUMMARY OF THE INVENTION

Skeletal muscle on a chip is a cantilevered rectangular beam that hangs horizontally and is not in contact with cell culture media. The cells contract and flex the rectangular beam upwards. In contrast, the In Vitro Contractile Force Indicator of the present disclosure has cylindrical cantilever beams that hang vertically. The polydimethylsiloxane (PDMS) beam flexes inwards while the 3D printed beam remains stationary. There are no in-vitro devices that measure cell contractile force.

The circular top allows the detector to be placed inside the in vitro testing well without calibration. For any tissue that has contractile nature, the device can be used to measure its force. There is no such current testing device using a non-rigid, or flexible post, which has cantilever beams hanging vertically into the cell or tissue culture medium. All current skeletal muscle on a chip designs have fixed rods and/or hang horizontally without contact in the medium.

In accordance with embodiments of the present disclosure, a device to measure the contractile force of a cell and/or tissue is disclosed. In one aspect, the device includes a mount with a rigid post sized to remain stationary and a non-rigid post sized to deflect based on forces exerted in the culture. The posts are disposed vertically within the cell culture or tissue medium. As the cells or tissues grow, they will constrict and flex the non-rigid post. The distance between the fixed rigid post and the post that flexed (non-rigid post) due to the cell or tissue growth is measured. This measurement information is used in the development of pharmaceuticals that affect cell or tissue growth.

In another aspect, the above device is made available in a kit. Pharmaceutical companies and/or individuals involved in drug research can purchase and customize the device. In an exemplary kit, the kit includes: 1 aluminum mold for PDMS fabrication of the non-rigid post, 1 ruler for measurements, and 3 in vitro devices.

In still another aspect, a method to determine the contractile force of a cell and/or tissue is disclosed. The method includes the steps of providing a rigid post and a non-rigid post within a well plate, and measuring the deflection of the non-rigid post. Cell and/or tissue contraction could be measured in real-time.

The device can be used in various aspects of research, such as drug development and the real-time measurement of forces from contractile tissues in in vitro culture. The device is sized to determine the force exerted within a cell population seeded within a hydrogel non-destructively, in real-time, using cantilever mechanics and a non-rigid post in one embodiment.

The above objects and advantages are met by the presently disclosed method and apparatus. In addition, the above and yet other objects and advantages of the present invention will become apparent from the hereinafter-set forth Brief Description of the Drawings, Detailed Description of the Invention, and claims appended herewith.

These features and other features are described and shown in the following drawings and detailed description. Furthermore, any combination and/or permutation of the embodiments are envisioned.

Again, other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

So that those having ordinary skill in the art will have a better understanding of how to make and use the disclosed composition and methods, reference is made to the accompanying figures wherein:

FIG. 1 is a diagram showing an assembly process and a device using a FORM2™ 3D printer, in accordance with one embodiment of the present disclosure;

FIGS. 2A-2B are computer aided design models of a 3D printed rigid post and a mount, showing a top perspective view and a bottom-up perspective view;

DETAILED DESCRIPTION

Figure 3:
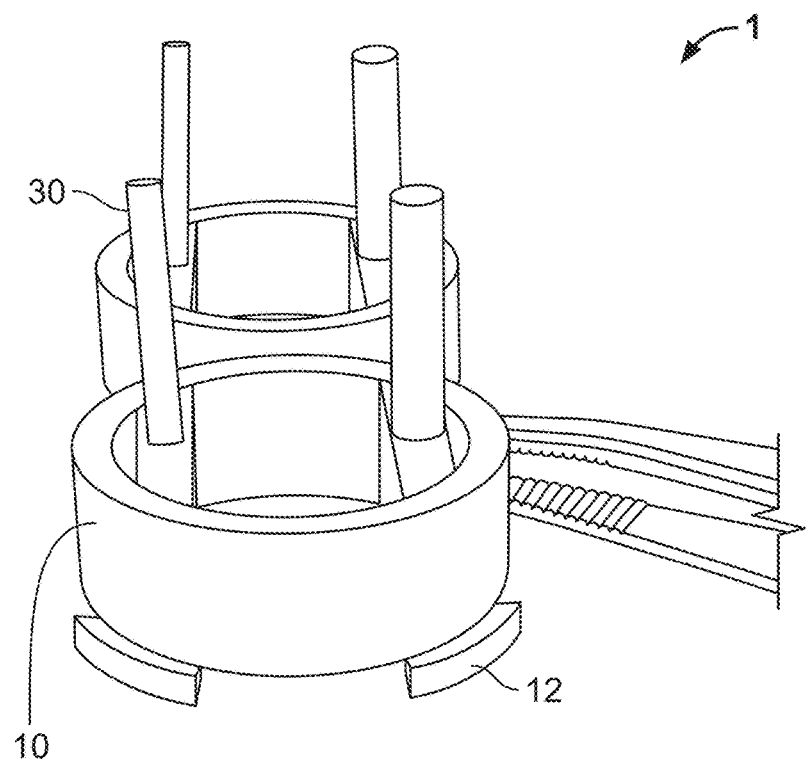
FIG. 3 shows the assembled contractile force indicator with the mount, rigid post, and attached non-rigid post.
Figure 4A:
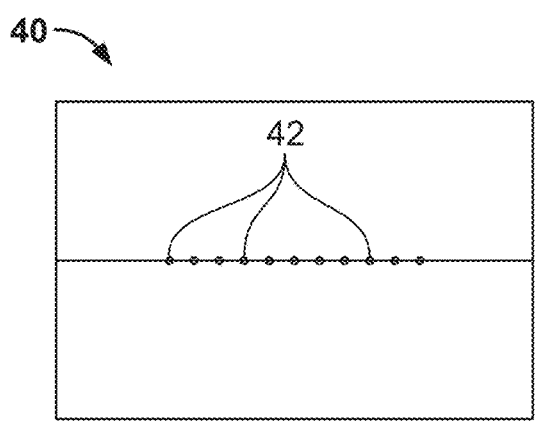
FIGS. 4A-4D show several views of an aluminum mold for the fabrication of non-rigid posts.
Figure 4B:
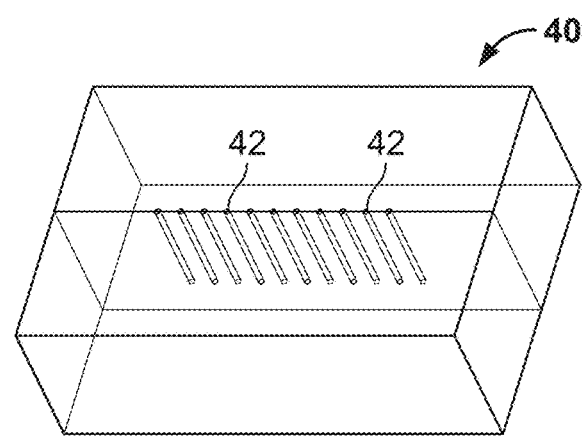
Figure 4C:
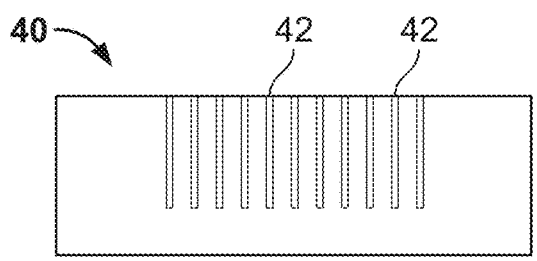
Figure 4D:
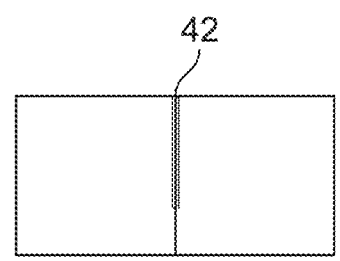

The In Vitro Contractile Force Indicator of the present disclosure functions using cantilever mechanics and a flexible polymer post, and is meant to be used with a well culture plate that grows cells and/or tissues. The device utilizes a rigid plastic material post and a non-rigid plastic material post attached to a mount. For purposes of this disclosure a rigid-plastic material is defined as a material exhibiting no elastic deformation such as but not limited to styrene polyblends, acrylic blends, polycarbonate, and the like. Such non-rigid plastic material are not prone to deflection when force is applied. Non-rigid plastic material is defined as an elastomeric material such as but not limited to rubber, polybutadiene, ethylene propylene rubber, ethylene propylene diene rubber, silicone elastomers, fluoroelastomers, polyurethane elastomers, and nitrile rubbers, and the like. Such non-rigid plastic material are prone to deflection when force is applied. The device takes into consideration that cells can exert forces around 32.91 µN to 47.27 µN, depending on the size of the tissue fabricated in the particular device. Further for purposes of this disclosure, a rigid post is one that would not deflect or deform when a force of at least 30 µN is applied. A non-rigid post is one that would deflect or deform when a force of at least 30 µN is applied.

Depending on the implementation the flexible or non-rigid post may be made of a polymer, such as polydimethylsiloxane (PDMS). PDMS has an elastic modulus of 360-870 kPa making this polymer ideal for flexing when a cell culture or tissue construct grows and constricts against the non-rigid post. Depending on the implementation the mount and rigid post may be made of a non-elastic rigid polymer including, but not limited to, nylon, polyacrylate, polycarbonate, and BIOMED AMBER RESIN™, (a strong, stiff rigid material composed by FormLabs™, the material is formulated for 3D printing and composed of a mixture of methacrylic esters and photo initiators) for biocompatible applications requiring short-term skin or mucosal membrane contact. Parts 3D printed with BIOMED AMBER RESIN™ are compatible with common solvent disinfection and sterilization methods), and the like. BIOMED AMBER RESIN™ is a mixture of 2-hydroxyethyl methacrylate, phenyl bis(2,4,6-trimethyl benzoyl)-phosphine oxide, and urethane dimethacrylate.

As further discussed herein, when the device is placed inside an individual well within a culture plate for testing of a cell culture or tissue construct, the non-rigid post such as a PDMS post will deflect towards the rigid post. The distance the PDMS post travels is measured by a specialized ruler. The distance can determine the forces contractile cells are exerting.

The In Vitro Contractile Force Indicator may be made available in a kit to allow researchers to build the device suitable to their specific research. In one implementation, the device is a combination of 3D printed and non-rigid such as PDMS parts. For the device, whether or not made available in a kit, there is a circular frame with tabs to allow the device to sit in a standard well plate. A standard well plate, may for example, include a 24 well such as an Eppendorf™ Cell Culture plate (polypropylene microplates). Each well for the plate may include an inside diameter of 16.5 mm and a depth of 17 mm. A typical well may hold between 0.5 mL/well to 1.0 mL/well and have a cell grow area of 208.9 mm2/well. The overall dimension of the plate with lid is 127.8×85.5×20 mm (l×w×h). The present invention is not limited to use in a 24 well culture plate, and may be used for example in a 12 well culture plate, or any culture plate regardless of the dimensions. The present invention may be adapted to fit any culture plate regardless of size dimension and the number of wells in the culture plate.

The materials and the methods of the present disclosure used in one embodiment will be described below. While the embodiment discusses the use of specific compounds and materials, it is understood that the present disclosure could employ other suitable compounds or materials. Similar quantities or measurements may be substituted without altering the method embodied below.

Depending on the implementation, the rigid post is 10 mm long with a diameter of 2 mm. The kit can include various post dimensions depending on the cell culture plate used. The flexible, non-rigid post may be PDMS, and the post may also have a dimension of 10 mm long by 1 mm diameter. This dimension can be varied to match the strength of the contractile tissue. While in the well plate, contractile cells will condense around the posts and the PDMS (non-rigid) post is pulled towards the 3D printed (rigid) post. By measuring the changing distance between these posts with a microscope, researchers can determine the force exerted by the cells in culture non-destructively, allowing for longitudinal studies assessing tissue health and strength over time.

One potential application of the In Vitro Contractile Force Indicator will help to discover drugs to treat muscular dystrophy. However, it is understood that applications may include any instance where cells that exert contractile forces, such as cardiomyocytes, smooth muscle cells, or fibroblasts, may be used with the present invention. This invention is not limited to use for any specific modality and may be utilized for several types of investigations including, but not limited to, different agents used in fighting several diverse types of diseases. This invention is placed inside a cell culture well, where hydrogels loaded with skeletal muscle cells will be cultured between the two posts, and used to determine the forces exerted by the contractile cells. Adding different reagents or drugs will determine which will positively impact muscular dystrophy. The In Vitro Contractile Force Indicator is round in shape with two posts protruding from the bottom. On the top, there are tabs to prevent the In Vitro Contractile Force Indicator from slipping into the cell medium, as well as allowing for the device to have a standardized position for the posts, which is important for imaging analysis.

There is a central window in the frame on the top to allow for access to the well to facilitate cell culture medium exchanges for long term studies. For best results, the In Vitro Contractile Force Indicator must be autoclaved and assembled under a biological hood, although assembly can take place prior to autoclave sterilization. Measurements are intended to be taken with an inverted microscope. The In-Vitro Contractile Force Indicator determines the force exerted by skeletal muscle cells in, for example, a 24-well plate. Again, the device preferably has two posts: one rigid and one non-rigid. The non-rigid post is fabricated for example from an elastomeric polymer such as PDMS using an aluminum mold. The PDMS may be casted in the aluminum mold or other such polymer processing. The mold allows the user to vary the dimensions as needed for the specific cell or tissue culture being evaluated. In the alternative, flexible rods of varying dimensions may be made available for the user to interchange on the mount as needed for the various testing of cell and tissue constructs.

Depending on the implementation, the rigid post and mount is fabricated using a 3D printer with BIOMED AMBER RESIN™ as previously described. The In-Vitro Contractile Force Indicator is designed to fit inside a single well with the posts directed downwards. The posts are attached to a 3D printed circular mount. The circular mount may have tabs to allow for a standard starting vertical position inside the cell culture plate well. The mount has a window to allow for media changes while the device is positioned inside the well.

In application, cells may be seeded in a hydrogel inside the cell culture plate well. As the hydrogel condenses, the cells wrap around the outside of the posts, pulling the non-rigid post toward the rigid post. A bottom-view light microscope is used to determine the deflection of the non-rigid post inside, for example, the 24-well plate. The movement of the non-rigid post is measured using a specialized acrylic ruler applied on the underside of the 24-well plate. The measurement of the ruler may be seen through the central window of the mount. The forces of the skeletal muscle cells may be determined using cantilever mechanics, for example, with an excel spreadsheet.

FIG. 1 is a diagram showing a method to produce a contractile force device 1 in accordance with one embodiment of the present disclosure. The contractile force device is sized to measure the forces exerted by contractile cells and/or tissues. The contractile force device could include a mount with a rigid post 14 and a non-rigid post 30. The rigid post and the non-rigid post are positioned downwardly from the mount. The rigid post is sized to serve as an anchor and a non-rigid post is sized to flex. It will be understood that other suitable anchors could be used.

The device having a two mount assembly with related components is designed to fit inside two adjacent wells within a multiwell culture plate to prevent rotation or movement during culture. For purposes of this disclosure and referred to herein, both mounts and rigid posts may have the same dimensions and may be made of the same material. For brevity, the mounts or first and second mounts and related first and second rigid posts, and first and second nonrigid posts, respective first and second set of tabs on the first and second mounts, first and second windows, and related components will just be referred to as the component name and not be referred to in the specification with the "first" and "second" identifiers unless there is a distinction to be made between components. For example, the non-rigid post may be made of a different material and/or different dimensions than its counterpart in the other mount so that when the two mount assembly with a first and second non-rigid post are disposed within wells in a multiwell culture plate various features may be evaluated for the same or different compound.

Depending on the embodiment, the rigid post and the mount could be fabricated using a 3D printer. The rigid post 14 could be part of the 3D printed component mount 10. The non-rigid post 30 could be fabricated from polydimethylsiloxane (PDMS). Although PDMS is the preferred material, it will be understood that other suitable flexible materials could be used. The non-rigid post could be attached to the device with any suitable connecting mechanism, such as cyanoacrylate adhesive. The contractile force device is sized to fit within one well of a for example, a Fisherbrand™ 24 (cell culture treated flatbottom microplate) well tissue culture multiwell, it will be understood that the device could be resized to fit in other multiwell sizes/configurations.

In one embodiment, the mount could have any suitable shape, such as a cylindrical shape, which aids in placement of the device within a well plate. The cylindrical mount 10 has a top edge 24 and a bottom edge 22. The top edge 24 of the cylindrical mount could include a plurality of tabs 12 to ensure the correct depth of the device 1 in a well plate 2. The tabs 12 ensure the depth by creating a lip 13 that sticks out further than the inside of a well 62 of the well plate, allowing the device 1 to sit on a top wall 66 of the well 62 in the well plate, physically fixing the device to a certain depth within the well.

Referring to again to FIG. 1, the non-rigid post 30 could be made by pouring PDMS into an aluminum mold 40 to obtain the correct post size. The 3D printer could be a FORM2™ (a desktop SLA (Stereolithography) 3D printer known for its high-resolution, accurate prints using liquid resin, making it suitable for detailed prototyping and production of parts with thin walls and intricate features), SLA, resin printer that is using from the company FormLabs™ a BIOMED AMBER RESIN™ (a biocompatible, rigid photopolymer resin formulated for 3D printing, composed of a mixture of methacrylic esters and photo initiators) to allow the unassembled printed device of the rigid post 14 and mount 10 to be autoclavable. These two parts, the non-rigid post 30 and the unassembled printed device of the rigid post 14 and mount 10, then are assembled together with the cyanoacrylate adhesive to make the device, which is autoclaved. Other assembly techniques may also be utilized such as sonic welding, heat welding, and the like. However, for case of operation for laboratory use, an adhesive is preferred. The assemble device 1 is then placed in an individual well 62 within the well plate 2 and seeded with a cell-loaded hydrogel. An acrylic ruler 50 could be affixed to the bottom of the well plate to allow the user to measure the distance measurement of how much the non-rigid post moves. The well plate and the ruler both could be imaged by microscope frequently and the forces exerted by the cells could be calculated.

In FIGS. 2A and 2B, although eight tabs 12 (four tabs per well) are shown, the number of tabs 12 could vary. Each tab could include a protrusion extending outwardly from the top edge 24 of the mount 10. In addition, a bridge 20 may connect two mounts at the top edge 24 of each mount. While the unassembled device shown in FIGS. 2A and 2B was designed to fit into two wells to prevent rotation or movement of the device and the corresponding posts, the number of wells a single device could fit into could vary. However, two mounts or more with associated rigid and non-rigid posts are preferable to be connected together to prevent rotation or movement of the device as the cell culture or tissue construct is growing and constricting the posts. The bottom edge 22 could have any suitable shape, such as circular, that serves to align the device in the well, so the posts line up with a ruler 50 and are in the middle of the well. The mount 10 could include a central window 18, which is the cut-out at the top of the mount 10. The window defines an opening in the mount. A first support member 25 and a second support member 26 are located within the mount. The first support member 25 is configured to hold the rigid post 14, and the second support member 26 is configured to hold the non-rigid post 30. The non-rigid post 30 is assembled into an opening 16 defined by the second support member 26.

With reference to FIGS. 2A and B and FIG. 3, the tabs 12 could be 3D printed on the mount 10 in one print. The tabs 12 serve to guarantee a standard depth of the device 1 within the well plate. The window 18 is sized to allow more light into the well to allow for easier observation and measurements of the ruler 50. The window 18 serves to allow for medium changes without removing the device from the well plate. For example, a pipette can easily be inserted through the window with disruption of the device and the progress of any investigation with the device. For one embodiment, it was determined that PDMS with a 15:1 weight ratio of elastomer base to curing agent yields an elastic modulus of 1.20±0.60 MPa after 1× autoclave.

The PDMS for the non-rigid post 30 could be mixed then poured into the aluminum mold 40; yielding a cylindrical post that is 10 mm in length and 1 mm diameter. It will be understood that the length and the diameter of the post could vary. A vacuum chamber could be used to ensure that the PDMS will fill the empty chambers of the mold. The aluminum mold with PDMS could be cured in an oven at 80° C. Then the non-rigid posts can be removed. For installation, the mount has a female socket for the male-non-rigid post to fit in. The non-rigid post allows the cells to wrap around both the rigid post 14 and non-rigid post 30, however, only the non-rigid post flexes. Based on how much the non-rigid post flexes determines the force of the cell contraction.

The rigid post and non-rigid post are the main calculation components of the device. The device is based on cantilever mechanics, where one post is deflected, and from that displacement, one can calculate the forces exerted. The rigid post serves as an anchor so the cell/tissue construct could wrap around two suspended posts. Once the cells start to condense around the device, the non-rigid post could deflect due to the contraction of the tissue. This deflection is used to calculate the force of contraction of the cells.

Referring to FIGS. 4A, 4B, 4C, and 4D, the mold 40 for the non-rigid post 30 could be made from an aluminum bar cut in half. The faces where both halves mate could be sanded to ensure a snug fit. The halves are secured tightly together before 11 drilled holes 42 (1 mm diameter) spaced 4 mm apart are made along the axis where both halves meet. The holes 42 are not drilled through the aluminum, but instead stop at a depth of 18 mm to allow the PDMS to fill the region. The two halves of the aluminum allows for case of removal of the posts due to the small dimensions of the components.

Figure 5:
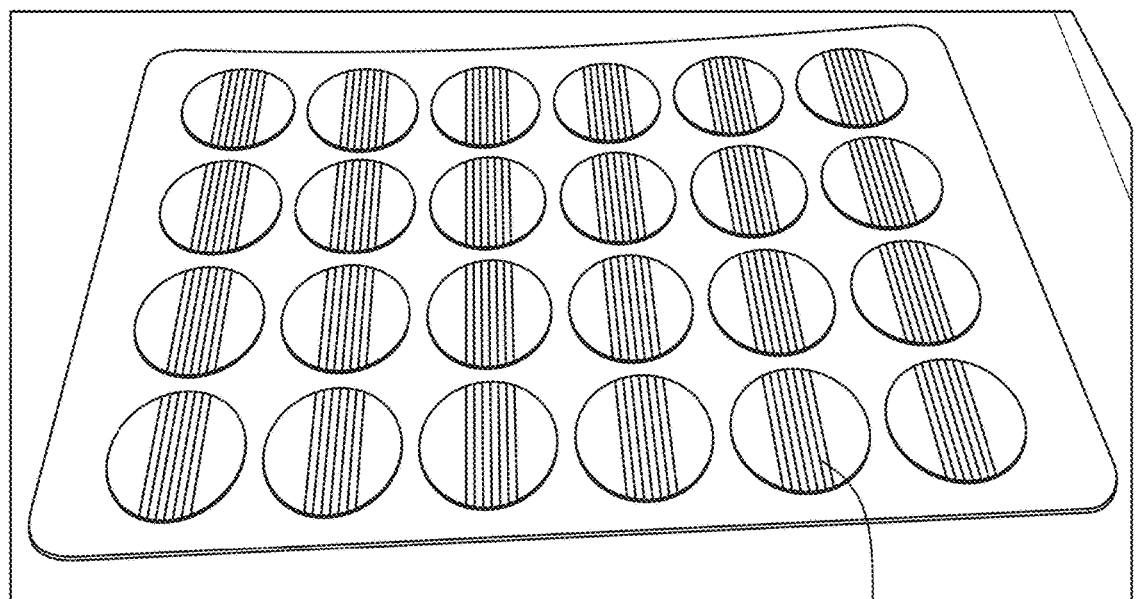
FIG. 5 is a photo of a laser engraved acrylic ruler.

With reference to FIG. 5, the ruler 50 could be laser engraved and cut from a transparent acrylic sheet whose thickness could be 1.6 mm. It is cut to size to fit on the underside of a 24 well plate. However, as previously shown the invention is adaptable to any size culture plate, including but not limited, to a 12 well culture plate or any other sized culture plate. Thus the ruler may be dimensioned to fit under the particular culture plate used. In any event, each well 62 is provided with its own ruler has marks 51 with vertical lines having a width of 0.035 mm and spaced 1.00 mm apart in one embodiment. The ruler is designed for bottom-up imaging. To measure deflection of the non-rigid post 30, an image is captured at day 0 and then subsequent days, as necessary. As the non-rigid post deflects, the non-rigid post will cross over hash marks 51. Computerized software could then be used to compare pixel locations at the specific times and therefore measure deflection.

Figure 6A:
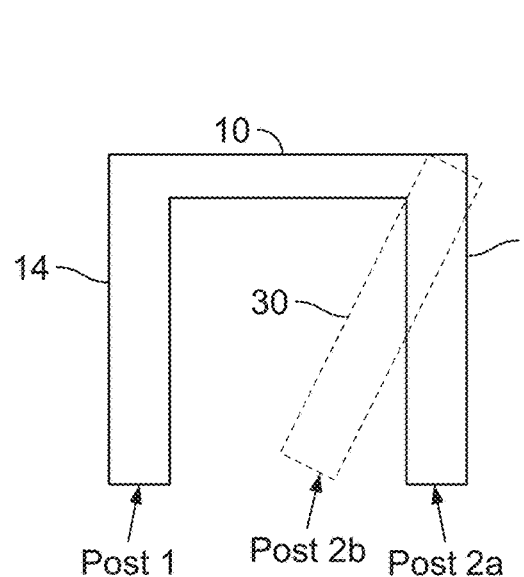
FIGS. 6A-6B are visualizations of the cantilever mechanics in this embodiment of the present disclosure.
Figure 6B:
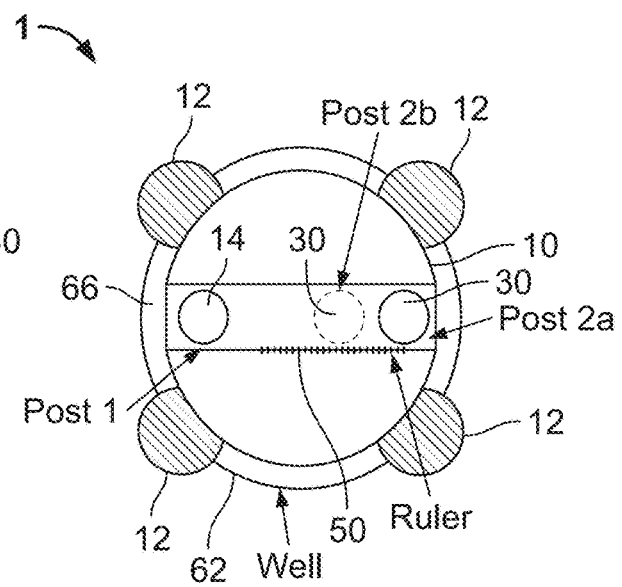

FIGS. 6A and 6B illustrate a simplified diagram showing the basic cantilever mechanics of the device. As the non-rigid post 30 (also labeled as Post 2a and Post 2b) moves toward the rigid post 14 (labeled as Post 1), the user can measure the change in distance and then use that distance change to calculate the force. The non-rigid post 30 will move towards the rigid post as the cells/tissue condense around the two posts in the hydrogel they are seeded within. As the cells/tissue condense, they will try to pull the two posts together; as one post cannot move, the non-rigid post will deflect towards the rigid post.

Figure 7A:
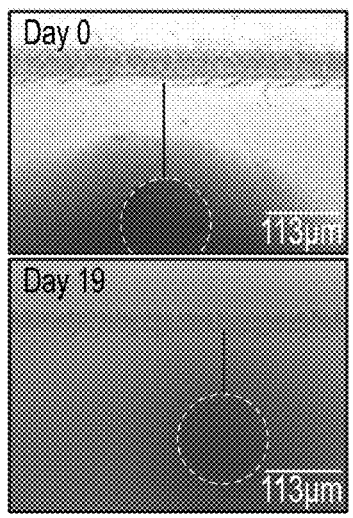
FIGS. 7A-7C show preliminary results of contraction from cell-populated hydrogels.

FIG. 7A demonstrates the use of the device in measuring the deflection of the non-rigid post during active culture. Cell-seeded hydrogels were injected around the device, and the position of the non-rigid post (outlined in the dotted white line) was measured with respect to the ruler.

Figure 7B:
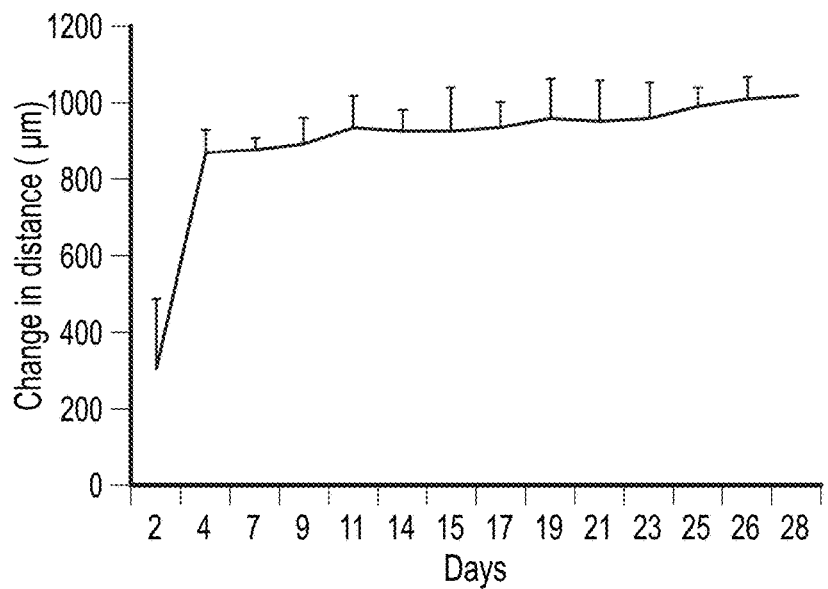

FIG. 7B visualizes the displacement of the non-rigid post, normalizing the location of the post with its original location at day 0. Data are presented as average±standard deviation, demonstrating the repeatability of the measurements of the device. In this embodiment, cells were seeded within a collagen hydrogel and the plot represents the displacement of the non-rigid post towards the rigid post, based on the measurements taken using the acrylic ruler and microscope. The non-rigid post was observed to rapidly deflect in the first 4 days of culture, and slowly continued to contract throughout the experiment.

Figure 7C:
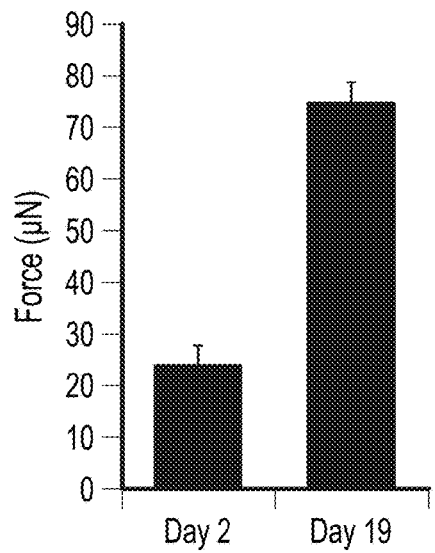

FIG. 7C displays the force values of data represented in panel B at days 2 and 19, using the cantilever mechanics described in Equation 1 below, and demonstrating the ability of this device to measure contractile forces from cells/tissue.

Figure 8:
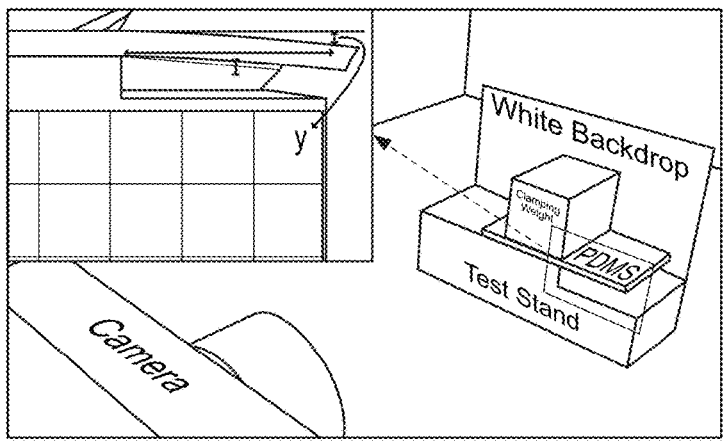
FIG. 8 illustrates a flexure test studio set up to determine Elastic modulus of the polydimethylsiloxane (PDMS) post.

FIG. 8 is an image of the set-up for the non-rigid post calibration. A sample of PDMS is evaluated in flexion before and after being autoclaved. The elastic modulus is found using Equation 2 below.

Figure 9:
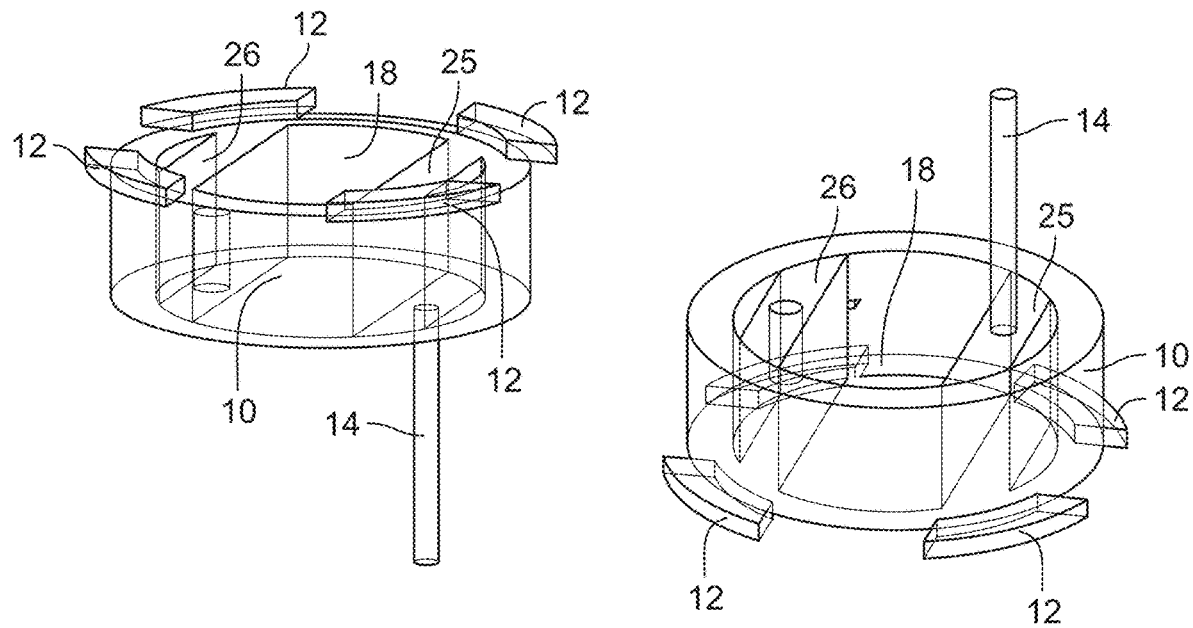
FIG. 9 illustrates one embodiment of a computer aided design model of a 3D printed rigid post and mount.
Figure 10:
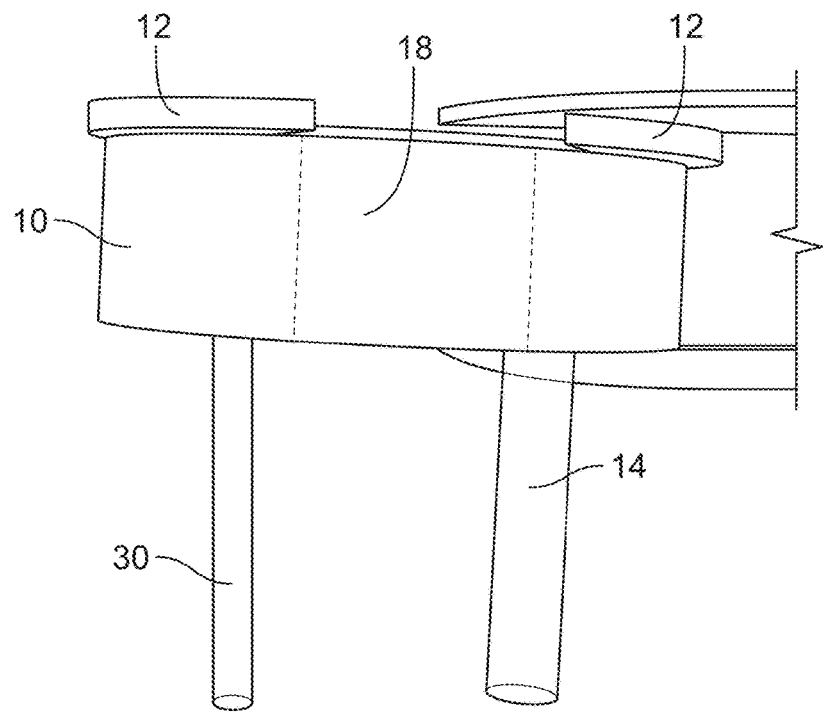
FIG. 10 illustrates one embodiment of the assembled contractile force indicator with the mount, rigid post, and attached non-rigid post.

FIG. 9 illustrates the device shown in FIG. 2A without the bridge 20. Similar numbers shown in FIG. 9 and FIG. 10 illustrate similar structural elements and similar functions previously shown and described herein. The advantage of utilizing a bridge as shown in FIGS. 2A-2B and FIG. 3 is that the device will not rotate relative to the ruler 50 as the culture grows and constricts about the rods of the device. However, the device may be utilized as shown in FIG. 9 and FIG. 10 without a bridge. If the user desires to further prevent rotation of the device in FIG. 9 and FIG. 10 mechanisms, such as, but not limited to, snap fits on the device and/or wells of the culture plate may be utilized. In addition, the device shown in FIG. 9 and FIG. 10 may be externally held in place by a brace, clamp, and/or adhesive material. These methods may be inconvenient to the user, and/or more expensive and cause inconsistencies in data recorded. The use of the bridge as shown in FIG. 2A and FIG. 2B and FIG. 3 provides at least an advantage of not utilizing such external means or adding snap fits or other securing mechanisms to prevent rotation of the device relative to the ruler as the culture grows about the posts.

The assembly of each component used in one embodiment is described below.

Non-Rigid Post Fabrication:
  a) Prepare PDMS solution at a 15:1 elastomer base to curing agent weight ratio.
  b) Pour onto aluminum mold and degas. Prepare additional samples for calibration.
  c) Cure PDMS at 80° C. for 30 minutes.
  d) Carefully remove PDMS posts from the mold.

Non-Rigid Post Calibration
  a) Prepared PDMS samples will be used for calibration.
  b) Determine the elastic modulus of samples using Equation 2 for both pre and post one autoclave cycle using the flexural test, as shown in FIG. 7.
  c) Before proceeding, input the correct modulus value into a booklet, which contains mathematical calculations, to ensure accurate force measurements.

3D Print Rigid Post and Mount
  a) Install BIOMED AMBER RESIN™ a mixture of 2-hydroxyethyl methacrylate, phenyl bis(2,4,6-trimethyl benzoyl)-phosphine oxide, and urethane dimethacrylate) into FORM2™ 3D printer (a desktop SLA (Stereolithography) 3D printer known for its high-resolution, accurate prints using liquid resin, making it suitable for detailed prototyping and production of parts with thin walls and intricate features).
  b) Turn on, load file and print device using the FORM2™ 3D printer.
  c) When print is complete, transfer into the IPA wash for 20 minutes. (1) Use IPA with 99% (v/v) concentration.
  d) Remove device from build plate and place in UV cure oven at 60° C. for 30 minutes.
  e) Remove the printed device from the cure oven and carefully remove the support material with tweezers.

Final Assembly
  a) Place cyanoacrylate adhesive on one end of the non-rigid post.
  b) Using tweezers, place the non-rigid post into the hole on the 3D printed device, opposite the rigid post.
  c) Allow 10 minutes for the adhesive to dry. d) Autoclave the fully assembled device to prepare for cell trials. The lab use of the device is described below.
  1. With the completed device in the well plate, place the acrylic ruler on the underside of the well plate.
  2. Inject a cell-seeded hydrogel within the wells where the device was placed.
  3. Place the well plate and ruler onto an inverted microscope stage.
  4. Take an image focused on the ruler.
  5. Without moving the microscope stage, take a second image focused on the post.
  6. Use an image processing program, such as ImageJ, to overlay the photos from steps 4 and 5. It is critical that the images acquired in steps 4 and 5 be taken without moving the construct on the microscope stage to ensure proper alignment of the ruler and the post for measurements taken in step 9.
  7. Record the starting point of the non-rigid post at day 0.
  8. Repeat steps 3 through 6 each day of the cell culture process.
  9. Using an image processing program, such as ImageJ, calculate the final displacement of the post. The final displacement of the post is the final position minus the starting position (an example of the results from these calculations is visible in FIG. 7B).
  10. After the post deflection is determined in millimeters, use a spreadsheet to determine the force exerted by the cells (FIG. 7C). The spreadsheet is written in terms of deflection and, therefore, the force corresponding to each deflection is the force the cells are exerting at that instance in time.

The elastic modulus of the PDMS provided within the spreadsheet is based upon initial testing of the device; however, it can be adjusted. By doing so, the spreadsheet will automatically update to provide an accurate force measurement.

Again, the device 1 could be used to study the effects of drugs, growth factors, or other soluble compounds; varying hydrogel compositions; or changes in cellular composition or phenotype on the mechanical output of cells cultured between the rigid post and the non-rigid post. The contractile force device could be used in vitro in a laboratory setting to determine the amount of force, at any instant, cells or tissues exert while growing within a hydrogel during culture.

A user could determine the concentration of cells seeded within a hydrogel solution (i.e., collagen type I or fibrin hydrogel, among others) to best suit the research. The cells seeded within the hydrogel will condense around the outside of the rigid and non-rigid posts of the device. As the cells grow and mature, they will both remodel the hydrogel matrix and contract; therefore, producing the mechanical force needed to pull the non-rigid post toward the rigid post.

Using contractile cells, such as myoblasts, which do not secrete their own matrix, can reduce the contribution of remodeled hydrogel matrix toward the mechanical measurements. However, if fibroblast-like cells are utilized in this device, these effects can be dissected by first measuring the distances between the posts prior ($F_{static}$) to, and immediately after, the incubation of the constructs with cytochalasin-D or another actin-disrupting compound to measure the residual forces ($F_{residual}$) and remove them from the calculations ($F_{cell}=F_{static}-F_{residual}$). Based on microscopy images taken on Day 0 and each day subsequently, the amount of deflection of the non-rigid post can be determined.

The final contractile force will be calculated using Equation 1; where L is the length of the non-rigid post, Δx is the measured deflection, r is the radius of the non-rigid post, and E is the elastic modulus determined by the sample's flexural test.

$$F(mN) = \frac{3(\Delta x)E\pi r^4}{4000L^3} \quad \text{(Equation 1)}$$

The elastic modulus (stiffness), E, is determined by a flexure test of the sample. For every batch of PDMS, a sample must be taken and evaluated for calibration of the system. In one embodiment, the flexure test of the sample could be performed before and after one autoclave cycle.

The stiffness may be calculated using Equation 2; where, E is the elastic modulus, w is the weight of the cantilever beam, L is the full length of the cantilever beam, I is the moment of inertia of the cantilever beam, and y is the deflection in the y direction.

$$E = \frac{wL^4}{8Iy} \quad \text{(Equation 2)}$$

Again, the device of the present disclosure allows researchers to study the effects of drugs, growth factors, or other soluble compounds; varying hydrogel compositions; or changes in cellular composition or phenotype on the mechanical output of cells cultured between the two posts. For example, myoblasts isolated from patients presenting with Duchenne's muscular dystrophy could be used within the contractile force device to measure the effects of different drugs or drug dosages on muscular strength or recovery.

In one embodiment, the elastic modulus of PDMS is a critical component of the contractile force device. The elastic modulus should be verified by a flexion test per each sample. This can be modified to best suit the users' research; however, the user should take into consideration that cells can exert forces around 32.91 µN to 47.27 µN, depending on the size of the tissue fabricated in the particular device and the particular cells that are used in the culture. While exemplary embodiments have been described herein, it is expressly noted that these embodiments should not be construed as limiting, but that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A contractile force indicator comprising:
a first mount having a cylindrical shape to fit inside a well of a culture plate that contains a growing specimen;
a first rigid post defined as having no deflection or no deformation when an external force of at least 30 µN is applied by the growing specimen, the first rigid post is integral to the first mount and the first rigid post remains stationary with respect to the first mount; the first rigid post is in a vertical position relative to the first mount; and the first rigid post is pointing in a downward direction into the well;
a first non-rigid post defined as having a deflection or a deformation when the external force of at least 30 µN is applied by the growing specimen; the first non-rigid post is interchangeably attached to the first mount and parallel to the first rigid post; and the first non-rigid post is pointing in the downward direction into the well;
wherein the first rigid post serves as an anchor when the first non-rigid post undergoes a deflection due to the external force of at least 30 µN applied by the specimen contracting and wrapping around the first rigid and the first non-rigid posts; and
wherein the deflection is for calculating a force of contraction of the specimen.

2. The contractile force indicator in claim 1, further comprising:
a ruler for measuring the deflection;
wherein the culture plate is a multiwell culture plate and the ruler is disposed underneath the multiwell culture plate during measurement;
the ruler further having a plurality of circular patterns to fit under each well of the multiwell culture plate; and
the plurality of circular patterns each further having a parallel pattern of hatch marks for measuring the deflection of the first non-rigid post.

3. The contractile force indicator of claim 1, further comprising:
a second mount having a second rigid post; the second mount connected to the first mount by a bridge portion;
wherein the first and the second mounts, the first and the second rigid posts, and the bridge portion are all integral; and
wherein the first and second mounts are inside two adjacent wells within a multiwell culture plate to prevent rotation or movement during culture of the specimen.

4. The contractile force indicator of claim 3, wherein the second mount includes a second non-rigid post that is a different dimension or a different material than the first non-rigid post.

5. The contractile force indicator of claim 3, wherein the second mount includes a second non-rigid post that is the same dimension as the first non-rigid post.

6. The contractile force indicator of claim 3, wherein the first mount further includes a first support and a second support; the first support having the first rigid post integrally attached thereon; the second support having a hole for interchangeable or for fixable attachment of the first non-rigid post.

7. The contractile force indicator of claim 6, wherein the first and the second supports define a window;
the window for allowing medium changes in each well of the multiwell culture plate without removal of the first mount from the multiwell culture plate; and the window for observing a ruler underneath the multiwell culture plate wherein the ruler has a circular pattern under each well; and the circular pattern further has a parallel pattern of hatch marks or vertical lines for measuring the deflection; and
wherein the vertical lines of the ruler having a width of 0.035 mm and spaced 1.00 mm apart.

8. The contractile force indicator of claim 7, wherein the ruler is transparent and allows bottom up imaging of the specimen in each well, wherein imaging is done starting at the bottom of each well in the multiwell culture plate.

9. The contractile force indicator of claim 8, wherein the specimen is a plurality of cells or tissue in a medium, wherein the cells or tissue contains myoblasts isolated from patients presenting with Duchenne's muscular dystrophy, and wherein the plurality of cells exert contractile forces, and the contractile force indicator measures effects of different drugs or drug dosages on muscular strength or recovery.

10. The contractile force indicator of claim 3, wherein each well of the multiwell culture plate contains varying hydrogel compositions; or varying cellular composition or phenotypes.

11. The contractile force indicator of claim 1, wherein the first mount, and the first rigid post are made of a mixture of 2-hydroxyethyl methacrylate, phenyl bis(2,4,6-trimethyl benzoyl)-phosphine oxide, and urethane dimethacrylate and the first non-rigid post is made of polydimethylsiloxane (PDMS) that are both autoclavable.

12. The contractile force indicator of claim 11, wherein the PDMS has an elastic modulus of 1.20±0.60 MPa after 1× autoclave.

13. The contractile force indicator of claim 1, wherein the specimen contains cells; and the deflection caused by cell forces constricting the first rigid and the first non-rigid posts as the cells grow is measured in real time.

14. The contractile force indicator of claim 1, where the first mount further includes a plurality of tabs to allow the first mount to sit in a multiwell culture plate; and dispose the first rigid and the first non-rigid posts into the specimen at the same distance.

15. The contractile force indicator of claim 1, wherein the first rigid post is 10 mm long with a diameter of 2 mm, and the first non-rigid post is 10 mm long.

16. The contractile force indicator of claim 15, wherein the diameter of the non-rigid post is changeable to match a strength of the specimen and wherein the specimen is contractile tissue.

17. The contractile force indicator of claim 16, wherein the non-rigid post is 1 mm diameter.

18. The contractile force indicator of claim 1, wherein the first mount and the first rigid post are 3D printed, and the first non-rigid post is cast in a mold.

\* \* \* \* \*